United States Patent
Boutaud et al.

(10) Patent No.: US 9,083,161 B2
(45) Date of Patent: Jul. 14, 2015

(54) ELECTRICAL FEEDTHROUGH IN A METAL WALL OF A HOUSING OF AN ACTIVE MEDICAL DEVICE AND METHOD OF MAKING THE SAME

(71) Applicant: SORIN CRM S.A.S., Clamart Cedex (FR)

(72) Inventors: Bertrand Boutaud, Paris (FR); Hélène Viatgé, Montrouge (FR)

(73) Assignee: SORIN CRM S.A.S., Clamart Cedex (FR)

( * ) Notice: Subject to any disclaimer, the term of this patent is extended or adjusted under 35 U.S.C. 154(b) by 110 days.

(21) Appl. No.: 14/034,366

(22) Filed: Sep. 23, 2013

(65) Prior Publication Data

US 2014/0020949 A1    Jan. 23, 2014

Related U.S. Application Data

(63) Continuation of application No. 13/069,177, filed on Mar. 22, 2011, now Pat. No. 8,539,670.

(30) Foreign Application Priority Data

Mar. 22, 2010   (FR) ..................... 10 52037

(51) Int. Cl.
*H02G 3/22* (2006.01)
*H02G 3/02* (2006.01)
*A61N 1/375* (2006.01)

(52) U.S. Cl.
CPC ............ *H02G 3/02* (2013.01); *A61N 1/3754* (2013.01); *Y10T 29/49155* (2015.01); *Y10T 29/49162* (2015.01); *Y10T 29/49165* (2015.01)

(58) Field of Classification Search
CPC ....... H02G 3/02; A61N 1/3754; A61N 1/375; A61N 1/08; A61N 1/3968; A61N 1/05; H01R 13/5224; H05K 1/112; A61B 5/042

USPC .......... 174/152 G, 650, 262, 50.56; 361/302, 361/307; 607/5, 9, 57, 62
See application file for complete search history.

(56) References Cited

U.S. PATENT DOCUMENTS 5,166,097 A    11/1992   Tanielian
5,322,816 A     6/1994   Pinter
(Continued)

FOREIGN PATENT DOCUMENTS

EP            1 177 815       2/2002
WO       WO-2008/067519       6/2008

OTHER PUBLICATIONS

Search Report for French Application No. FR0958137 FA730043, mail date Apr. 15, 2010, 2 pages.

*Primary Examiner* — Hoa C Nguyen
*Assistant Examiner* — James Wu
(74) *Attorney, Agent, or Firm* — Foley & Lardner LLP

(57) ABSTRACT

A method for making an hermetic and electrically insulating feedthrough in the metal wall of a housing of a device, preferably of an active medical device, is disclosed. The method includes: a) forming electrically insulating layers (24, 26) on each of the internal and external sides of the wall (10), b) on the internal side of the wall, forming a non-through groove with a closed contour (30) defining in the wall a metal islet (28) that is physically and electrically isolated from the rest of the wall, by removing the entire thickness of the electrically insulating internal layer (26) and the wall (10), leaving intact a sufficient thickness of the electrically insulating external layer (24) so that the external layer mechanically supports the metal islet, and c) on the external and internal sides respectively, exposing pads (34, 36) for making an electrical contact to the metallic islet, by a localized removal of material of the electrically insulating external and internal layers (24, 26), respectively.

20 Claims, 2 Drawing Sheets

(56) References Cited

U.S. PATENT DOCUMENTS

| | | |
|---|---|---|
| 5,751,539 A * | 5/1998 | Stevenson et al. ............ 361/302 |
| 5,905,627 A * | 5/1999 | Brendel et al. ................ 361/302 |
| 6,091,027 A | 7/2000 | Hesselbom et al. |
| 6,110,825 A | 8/2000 | Mastromatteo et al. |
| 6,456,481 B1 * | 9/2002 | Stevenson .................... 361/302 |
| 6,574,508 B2 | 6/2003 | Zaouali et al. |
| 7,035,076 B1 * | 4/2006 | Stevenson .................... 361/302 |
| 7,489,495 B2 * | 2/2009 | Stevenson .................... 361/302 |
| 7,557,679 B2 | 7/2009 | Martin et al. |
| 7,725,190 B2 | 5/2010 | Iyer et al. |
| 8,062,074 B2 | 11/2011 | Ries et al. |
| 8,129,622 B2 | 3/2012 | Taylor et al. |
| 2007/0112396 A1 | 5/2007 | Dalton et al. |
| 2011/0230937 A1 | 9/2011 | Boutaud et al. |

\* cited by examiner

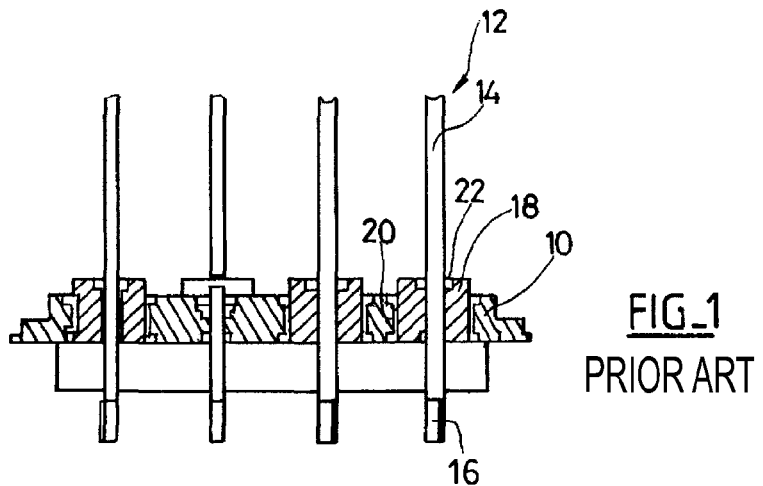
FIG_1
PRIOR ART
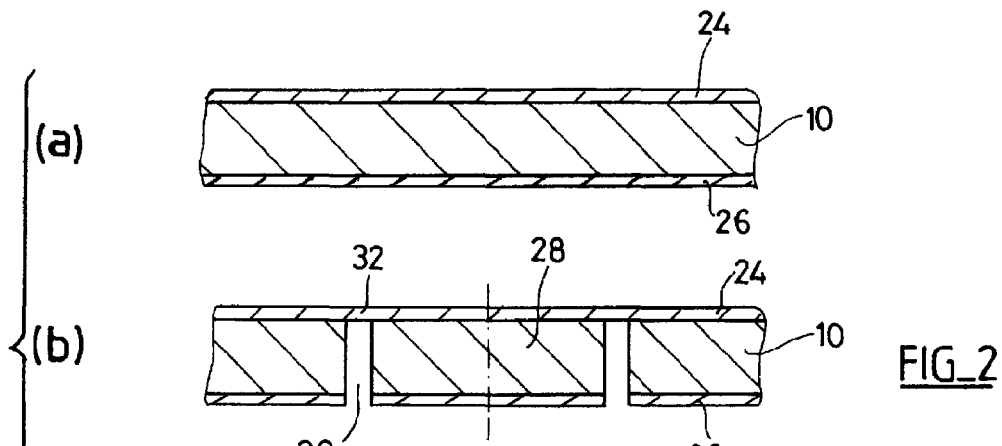
FIG_2
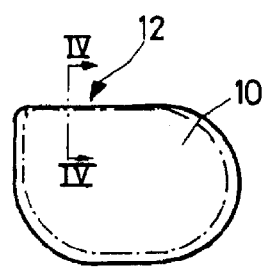
FIG_3
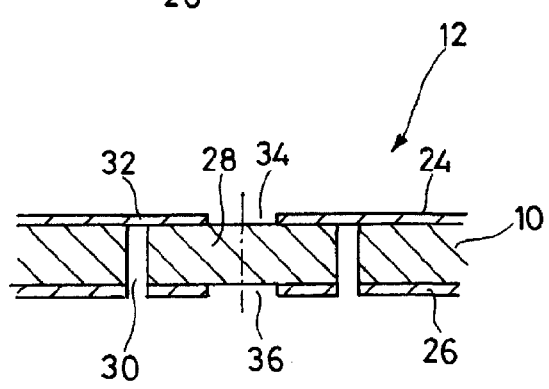
FIG_4

FIG_5
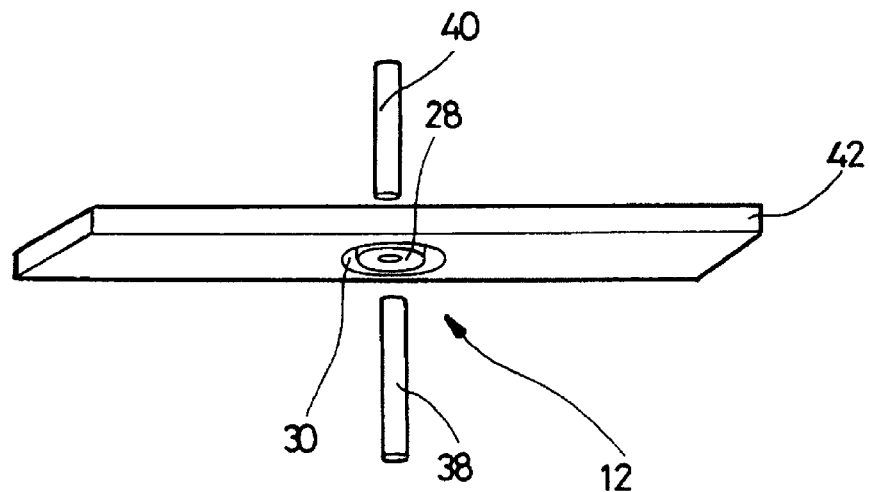
FIG_6
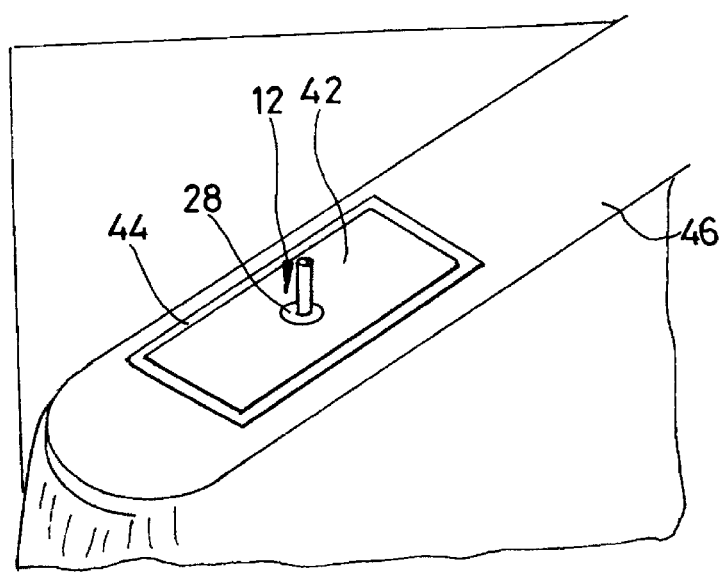

ly to devices that continuously monitor the cardiac activity of a

ELECTRICAL FEEDTHROUGH IN A METAL WALL OF A HOUSING OF AN ACTIVE MEDICAL DEVICE AND METHOD OF MAKING THE SAME

RELATED APPLICATIONS

This application is a continuation application claiming the benefit of and priority to U.S. patent application Ser. No. 13/069,177 filed Mar. 22, 2011, which claims the benefit of French Application No. 1052037 entitled "Method for making an electrical feedthrough in the metal wall of a housing, notably of an active medical device, and device provided with such a feedthrough" and filed Mar. 22, 2010. Both U.S. patent application Ser. No. 13/069,177 and French Application No. 1052037 are hereby incorporated by reference in their entireties.

FIELD OF INVENTION

The present invention relates to "active implantable medical devices" as defined by the Jun. 20, 1990 directive 90/395/CEE of the European Community Council, and particularpatient and deliver to the patient's heart, if necessary, electrical pulses for stimulation, cardiac resynchronization, cardioversion and/or defibrillation pulses in the case of a rhythm disorder detected by the devices, as well as to other types of devices such as neurological devices, cochlear implants, devices for making a pH measurement, and devices for detecting other intracorporeal parameters. It can also be applicable to any electronic device and to any component requiring a feedthrough, such as batteries, capacitors, etc.

BACKGROUND

Active implantable medical devices typically have a generator that has a metal housing, typically made of titanium, on which a connector head is mounted. The connector head, also referred to as simply a connector, is provided to mechanically and electrically connect the generator to one or more leads. The leads have at their distal end various electrodes used for sensing electrical activity signals of the patient and delivering stimulation pulses, e.g., pacing and defibrillation to the patient's heart.

The connection of the connector head to various electronic circuits enclosed in the generator housing involves establishing several feedthroughs in the housing. Each of the feedthroughs has a pin conductor to be connected to a corresponding plug of the connector head at its one end emerging from the upper surface of the housing (i.e., on the outer or external side), and to be connected to the electronics at its other end emerging from the surface of the housing opening into the interior volume of the housing (i. e., on the inner or internal side) where the electronic circuits are located.

One type of feedthrough structure is described, for example, in EP 1177815 A1 and its counterpart U.S. Pat. No. 6,574,508 (both assigned to Sorin CRM S.A.S, previously known as ELA Medical). In addition to the connection pins on the connector head, other feedthroughs are provided, for example, to provide a connection with a surface electrode placed on the outside of the housing.

These feedthroughs can also be found in other sub-components of active medical devices such as batteries and capacitors.

It is important that a feedthrough must electrically isolate the particular conductor passing through the metal housing and also form an hermetic seal to prevent penetration of body fluids into the housing, throughout the life of the implanted device, typically for ten years. Therefore, a feedthrough is a key element in design of the housing of active implantable devices, particularly defibrillators and pacemakers, for providing a dual function of electrical current flow and of sealing of the housing.

For electrical isolation, dielectric materials such as ceramic or glass are used to form highly resistant mechanical connections with the metal of the housing. To this end, the insulating material of the feedthrough is surrounded by a metal collar and welded to the housing of the device, or to the half-housing prior to two half housings being joined together. The connections between the pins and the insulating material are made hermetic by brazing with a suitable material, such as gold, in the interface area to ensure complete sealing and insulation.

The complexity of the formation of these feedthroughs and the use of specific components and technologies are partly attributed to the high price of the feedthroughs, which may contribute up to 10% of the total cost of a device. In addition, the current trend of increasing the number of electrodes (e.g., in "multisite" devices) requires an increase in the number of contacts on the connector, and the number of pins, consequently increasing the cost of forming of the feedthroughs.

Other challenges remain with existing techniques for forming feedthroughs. In particular, due to the fact that the feedthrough is integrated into the housing, the hermetic seal of the housing that is made of titanium, is generally performed by laser welding, which is a complex and costly operation because it may introduce gaps, both vertically and horizontally, sometimes too large for the laser welding to be effective.

Furthermore, when integrated to the housing, the feedthroughs may undergo significant thermomechanical stresses during laser welding due to its heterogeneous structure and present reliability and reworking concerns.

Furthermore, feedthroughs require a grouping of electric wires, therefore they must be sized appropriately to accommodate the wire pins. As these electrical wires are to be connected to the connector head at points of contact that are spaced apart, it is necessary to impose relatively large curvatures to the electrical pins coming out of the feedthrough, to direct the wire pins to the appropriate points of contact on the connector head.

These important roles and features of feedthroughs inside and outside of the housing severely limit the degree of miniaturization during the device design.

Although the currently known feedthroughs adequately fulfill their intended functions (e.g., hermeticity and transfer of the electrical signals), they contribute a large share of manufacturing cost to implantable medical devices, which is not only a constraint in the design of such devices but also a limitation to miniaturization and a significant source of reliability defects during the assembly of the housing. These difficulties have not yet been appropriately overcome.

Various alternative techniques have been proposed, but they are relatively complex and have drawbacks.

U.S. Pat. Publication No. 2007/0112396 A1 describes a technique for forming a feedthrough for an implantable medical device such as a cochlear prosthesis. The feedthrough is made to be conductive by locally doping silicon on selected paths, instead of making a driver (pin) to extend from one side of the feedthrough. One difficulty with this structure lies in the absence of physical isolation of the area of electrical conduction, because the interface between doped silicon and undoped silicon is not completely insulated. In addition, this technique requires the transfer of a silicon wafer to the device housing to manufacture the feedthrough. It requires silicon/titanium brazing that has roughly the same drawbacks and difficulties of the ceramic/titanium brazing technique as mentioned above.

U.S. Pat. Publication No. 2007/0060969 A1 proposes to make the feedthrough by stacking a number of layers of green ceramic provided with staggered vias that are interconnected by a conductive adhesive applied between the number of layers. However, this technique has the same drawbacks as the previous technique lacking physical separation between insulating and conductive materials (although in this case, the materials are different), and requiring an assembly of the ceramic feedthrough on the titanium case by a hermetic brazing. In addition, the manufacturing cost is relatively high because of the relatively complex operations and the use of ceramics and conductive materials of platinum/iridium or gold.

In areas (including aeronautics) other than medical implants, other feedthrough techniques have been proposed, for example, as described in U.S. Pat. Nos. 5,166,097 A and 5,322,816 A. But these feedthroughs are made from a silicon wafer that is applied later on the metal housing with technological constraints and difficulties involved in such an operation.

OBJECT AND SUMMARY

It is therefore, an object of the present invention to provide electrical continuity via a feedthrough between the internal and external sides of a housing while providing an hermetic sealing and electrical insulation with the housing. It is further an object to avoid use of a ceramic/metal component and the difficulties of laser welding the ceramic/metal component to a housing due to vertical and horizontal gaps.

According to one embodiment, a zone dedicated to the electrical conduction is created in the mass of the housing wall in the region of the feedthrough. This zone of electrical conduction is physically electrically isolated from the rest of the housing.

In order to employ solidarity and integration of the isolated zone with the rest of the housing while providing hermetic sealing to prevent body fluids to enter through the isolated zone, an isolating layer is added on the housing, for example, by oxidation of the metal surface of the housing or by deposition of a silicon dioxide layer.

One embodiment of the present invention is directed to a method for forming an hermetic and electrically isolating feedthrough, allowing an electrical connection to pass through the housing wall of a device, in the following steps:

a) forming an electrically isolating layer on each of the external and internal sides of the metallic electrically conductive housing wall of the device;

b) on the internal side of the housing wall, forming a groove having a closed contour delimiting a metallic islet that is physically and electrically isolated from the rest of the housing wall, by removing the electrically isolating internal layer and by digging through all the thickness of the housing wall, while leaving at least substantially intact thickness of electrical isolation from external layering. The groove is referred to as a "non-through groove" in that the groove does not pass completely through the housing wall, and the external layer mechanically supports the metallic islet; and c) exposing, on the external and internal sides respectively, a pad to make an electrical contact with the metallic islet, by locally removing some material on the thickness of the electrically isolating external and internal layers.

According to one embodiment, the electrically insulating layer formed in step a) is obtained by oxidizing the metal surface of the housing wall over a portion of the thickness of the wall, or by depositing an additional layer of electrically insulating material on the surface of the housing wall.

According to one embodiment, the non-through groove with a closed contour formed in step b) is obtained by a technique selected from among of a group consisting of: chemical selective etching, selective physical etching, laser engraving, precision sawing, and any combination of the foregoing.

The method may also include a step of: d) welding electrical conductors to the pads for forming external and internal electrical contacts, so as to form said electrical connection.

The method for forming an hermetic and electrically isolating feedthrough may further include a step of injecting an electrically insulating filler material in the non-through groove that has a closed contour as formed in step b).

According to one embodiment, steps a) to c) are executed directly on the housing wall of a device, or on a separate component of the device housing. In the latter case, the method may further include a step of applying and securing of the separate component on the rest of the device housing.

Another embodiment of the present invention is directed to an active medical device having a housing made according to one of the above method(s). Specifically, such a housing includes a metal wall having an external side and an internal side and supporting at least one hermetic and electrically insulating feedthrough for the passage of an electrical connection through the metal wall.

On the internal side, the housing wall includes an internal electrically insulating layer on the internal surface of the wall, and a non-through groove with a closed contour delimiting an islet in the metal wall that is physically and electrically isolated from the rest of the wall, and a pad for use as an electrical contact to the metallic islet, the electrically insulating internal layer being absent in the region of the pad for making an electrical contact. The non-through groove extends through the entire thickness of the electrically insulating interior layer and the housing wall, leaving essentially intact the thickness of the electrically insulating external layer On the external side, the housing wall includes an external electrically insulating layer and a pad for an electrical contact to the metallic islet. The electrically insulating external layer is absent in the region of the pad for electrical contact leaving intact a sufficient thickness of the electrically insulating external layer so that the external layer can mechanically support the metal islet. Optionally, the electrically insulating external layer can be removed except in the region needed to support the metal islet, for example, for a device external housing that is to be used as an electrode in a pacing vector. An electrically insulating filler material may be used to fill the external non-through groove with a closed contour.

The housing wall may be an integral part of the an active medical device, or a separate component that is applied on an existing active medical device housing.

BRIEF DESCRIPTION OF THE DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements, and in which:

FIG. 1 is a sectional view of a feedthrough, according to the prior art;

FIG. 2 illustrates successive steps of a process for forming a feedthrough, according to one embodiment of the present invention;

FIG. 3 is a general view of a device housing provided with a feedthrough, according to one embodiment;

FIG. 4 is a sectional view taken along the line IV-IV of FIG. 3, at the feedthrough level;

FIG. 5 is a perspective view, from below, of an embodiment of the present invention in which the feedthrough is formed on a separate component; and FIG. 6 is a perspective view from above of the separate component of FIG. 5 welded to a device housing.

DETAILED DESCRIPTION

With reference to the drawings, various embodiments according to the present invention will now be described.

FIG. 1 illustrates a feedthrough of the prior art. Reference 10 designates the metal housing of a generator (or alternatively a separate metal component, e.g., titanium, that will later be applied to the housing), with a plurality of feedthrough pins 12. Feedthrough pins 12 have one end 14 that terminates on the outside of the housing, for connection to a contact part of a connector head, and an opposite end 16 that is intended to be connected to contact wires, for connection with the internal circuitry of the generator. These feedthrough pins 12 are generally made of platinum or iridium, and are insulated from the housing 10 by an insulating element 18 that is commonly made of ceramic or glass. Each insulating element 18 is ringed with a metal collar 20 to ensure an hermetic attachment to the titanium housing 10 by gold brazing. The pins 12 are also secured to the insulating element 18 by a gold brazing at 22.

FIG. 2 illustrates successive steps of a process for forming a feedthrough, according to one embodiment of the present invention. Essentially, the present invention dispenses with an intermediate component (such as the ceramic insulating element 18 of conventional feedthroughs) to provide an isolated area in the thickness of the housing wall to ensure electrical conduction. The formation of this area, herein referred to as an "islet" requires consideration of the following conditions, including:

the thinness of the wall of the titanium housing, which is typically about 300 microns;

the biocompatibility and biostability of the housing, as well as its resistance to corrosion;

the fragility in the region of feedthroughs, as this region is likely to be manipulated by operators during the assembly of the device;

the compatibility of the new technique with the steps of assembling the device upstream and downstream in the production chain;

the resistance to the different processes used such as laser welding and gluing of the connector head.

To this end, the feedthrough forming technique of the present invention provides a first step as illustrated in FIG. 2a, of creating on both internal and external sides of the titanium housing wall 10 an external insulating layer 24 and an internal insulating layer 26. These insulator layers can be produced by oxidation of the titanium housing wall 10 to a controlled depth, or by depositing a layer of insulating material, e.g., silicon dioxide, on the corresponding surface of the titanium housing wall 10. The thickness of each layer 24 and 26 is, for example, 10 microns, for a thickness of the housing wall of about 300 microns. Other suitable dimensions may be used depending on the choice of material, the processing of forming the insulator layers, and/or the condition under which the device is to be used.

These layers 24 and 26 may be made, for example, by thermal oxidation, or any other method such as plasma oxidation or chemical deposition. It is possible to proceed by anodization, by submitting the case to a potential difference and by simultaneously putting it in contact with a solution of water and sulfuric acid, either by soaking or by using an electrode brush.

The next step, as illustrated in FIG. 2b, is to make a physically isolated conductor islet 28 in the thickness of the housing wall by removing material to make a non-through groove 30. In the direction of depth, the groove 30 is formed from the internal side through the entire thickness of the internal insulating layer 26 and the entire wall thickness of the metal housing 10. In contrast, the external layer 24 is left essentially intact, so that the islet 28 can be mechanically supported by the bridge 32 formed by the external layer between the isolated area 28 and the rest of the metal layer of the housing 10. The external layer 24 also forms a hermetic barrier between the inside of the housing 10 and the outside environment.

In the plane of the housing surface, the groove 30 is cut to form a closed contour, so as to completely electrically isolate the islet 28 from the rest of the housing 10 along its periphery. The islet 28 remains, however, mechanically connected to the rest of the housing 10 by bridges 32 of the external insulating layer 24 formed in the previous step.

The formation of the groove 30 can be achieved by various known techniques. For example, selective chemical etching (e.g., interactions of reactive elements with titanium), physical etching (e.g., ion bombardment), or any micro-structuring means such as accurate sawing may be used. Other techniques for forming semiconductors and the micro-electromechanical systems (MEMS), plasma etching (RIE, Reactive Ion Etching), or TIDE (Titanium Inductively-Coupled plasma Deep Etching) can also be used. It is further possible to use laser engraving, chemical etching by soaking the titanium or the insulating layer in a acidic or basic chemical solution (depending on the material to be removed), with selective masking of the non-etched area. These techniques can also be combined and/or sequenced to minimize the time to cut through the titanium to form the groove 30.

The next step, as illustrated in FIG. 2c, is to selectively achieve the openings 34 and 36 in the respective insulating layers 24, 26 so as to expose the pads or areas on which the wires or pins can be brazed to ensure electrical contact with the conductive islet 28. These openings 34, 36 can be achieved by selective chemical etching, for example, reactive ion etching (RIE). The dimensions are chosen to allow an easy realization of the contact with a pin or with an electrical conductor, however, leaving on the external side enough material of the exterior layer 24 to avoid weakening the structure in the region of the bridge of material 32 that mechanically supports the islet 28.

Optionally, the volume where material was removed corresponding to the groove 30 can be filled with an electrically insulating filler material such as a glue or a resin of a type commonly used for electronic chips. The insulating filler material will function to: overcome any fragility of the material resulting from the various loads made thereto provide an additional electrical isolation of the conductive islet 28, and increase the overall hermeticity of the structure.

FIG. 3 and FIG. 4 show the top and sectional views of the device housing provided with a feedthrough implemented in accordance with the processes of FIGS. 2a to 2c. The feedthrough may be implemented directly on the housing 10 or on a part the housing, for example, the part referred to as a half-can. The direct implementation of the feedthrough 12 on the housing 10 circumvents the assembly steps of the feedthrough, thus significantly reduces the manufacturing cost and the time of manufacture.

FIG. 5 and FIG. 6 illustrate an alternative embodiment in which the feedthrough 12 is made on a separate component. Feedthrough 12 is applied on the separate component and secured to the housing of a device later. FIG. 5 shows the feedthrough 12 that has a structure identical to that of FIG. 4 with inner pin 38 and outer pin 40 ready to be connected by brazing to the isolated conductive islet 28. The difference lies in the fact that the feedthrough 12 is not realized on the case of the housing itself, but on a titanium plate 42 that is integrated with and secured to the rest of the housing 46 by a peripheral brazing as shown in FIG. 6.

This variant facilitates the construction process, because it is easier to manufacture a feedthrough on a flat piece of a small sized plate, such as the plate 42 of FIGS. 5 and 6, instead of directly implementing on the housing wall 10. It involves an additional step of welding along the line 44 between the plate 42 and the housing 46, but this is a titanium-to-titanium weld between two identical materials, therefore it does not suffer from the problems of thermal expansion encountered with the welding of dissimilar materials such as a ceramic/titanium interface of prior art feedthroughs.

One of ordinary skill in the art will appreciate that the present invention may be practiced by other methods and sequences than the embodiments described above, which are presented for purposes of illustration and not of limitation.

What is claimed is:

1. A hermetic and electrically insulating feedthrough for an electrical connection through an electrically conductive metal wall, the feedthrough comprising:
   an electrically insulating external layer on an external side of the electrically conductive metal wall;
   an electrically insulating internal layer on an internal side of the electrically conductive metal wall;
   a non-through groove on the internal side of the electrically conductive metal wall, the non-through groove having a closed contour defining a metal islet in the electrically conductive metal wall, wherein the metal islet is physically and electrically isolated from the rest of the electrically conductive metal wall;
   an external pad on the external side of the electrically conductive metal wall, the external pad making electrical contact to the metal islet; and
   an internal pad on the internal side of the electrically conductive metal wall, the internal pad making electrical contact to the metal islet.

2. The feedthrough of claim 1, wherein the non-through groove extends through an entire thickness of the electrically insulating internal layer and through an entire thickness of the electrically conductive metal wall, leaving the electrically insulating external layer intact to have a thickness sufficient to mechanically support the metal islet.

3. The feedthrough of claim 1, wherein the electrically insulating internal layer and the electrically insulating external layer are formed by oxidizing the internal side and the external side of the electrically conductive metal wall.

4. The feedthrough of claim 1, wherein the electrically insulating internal layer and the electrically insulating external layer are formed by depositing an electrically insulating material on the internal side and the external side of the electrically conductive metal wall.

5. The feedthrough of claim 1, further comprising:
   electrical conductors welded on the external pad and the internal pad to form said electrical connection through the electrically conductive metal wall.

6. The feedthrough of claim 1, further comprising:
   an insulating filler material filling in the closed contour of the non-through groove.

7. The feedthrough of claim 1, wherein the electrically conductive metal wall is a housing wall for an active medical device.

8. The feedthrough of claim 1, wherein the electrically conductive metal wall is component separate from a housing wall for an active medical device; and
   wherein the electrically conductive metal wall is applied and secured to the housing wall for the active medical device.

9. The feedthrough of claim 1, wherein the non-through groove is formed by a technique selected from among a group consisting of: chemical selective etching, physical selective etching, laser engraving, precision sawing, and any combination of the foregoing.

10. A housing for a device, the housing comprising:
    a metal wall having an external side and an internal side;
    a hermetic and electrically insulating feedthrough for an electrical connection through the metal wall;
    an electrically insulating internal layer formed on the internal side of the metal wall;
    a metal islet defined by a non-through groove having a closed contour, the metal islet being physically and electrically isolated from the metal wall, the non-through groove extending through an entire thickness of the electrically insulating internal layer and through an entire thickness of the metal wall; and
    an electrically insulating external layer formed on the external side of the metal wall, wherein the electrically insulating external layer is left intact to have a sufficient thickness to mechanically support the metal islet.

11. The housing of claim 10, further comprising:
    a first pad for making electrical contact to the metal islet from the internal side of the metal wall, the electrically insulating internal layer being absent in the region of the first pad for electrical contact; and
    a second pad for making electrical contact to the metal islet from the external side of the metal wall, the electrically insulating external layer being absent in the region of the second pad for electrical contact.

12. The housing of claim 10, further comprising:
    an insulating filler material disposed in the closed contour of the non-through groove.

13. The housing of claim 10, wherein the metal wall is integral with an active medical device housing.

14. The housing of claim 10, wherein the metal wall is a separate component applied to a housing of an active medical device.

15. The housing of claim 10, wherein the electrically insulating internal layer and the electrically insulating external layer are formed by depositing a layer of an electrically insulating material on the internal side and the external side of the metal wall, respectively.

16. The housing of claim 10, wherein the non-through groove is formed by a technique selected from among a group consisting of: chemical selective etching, physical selective etching, laser engraving, precision sawing, and any combination of the foregoing.

17. A feedthrough comprising:
    an electrically conductive wall having an internal side and an external side, wherein a portion of the electrically conductive wall is electrically isolated from a remainder of the electrically conductive wall;

an electrically insulating internal layer on the internal side of the electrically conductive wall, wherein the electrically insulating internal layer is absent in a region on the internal side of the portion of the electrically conductive wall that is electrically isolated from the remainder of the electrically conductive wall; and an electrically insulating external layer on the external side of the electrically conductive wall, wherein the electrically insulating external layer is absent in a region on the external side of the portion of the electrically conductive wall that is electrically isolated from the remainder of the electrically conductive wall;

wherein the portion of the electrically conductive wall that is electrically isolated from the remainder of the electrically conductive wall is configured to form an electrical connection through the electrically conductive wall.

18. The feedthrough of claim 17, wherein the portion of the electrically conductive wall that is electrically isolated from the remainder of the electrically conductive wall is defined by a closed contour groove extending through an entire thickness of the electrically conductive wall.

19. The feedthrough of claim 18, wherein the closed contour groove extends through an entire thickness of either the electrically insulating internal layer or the electrically insulating external layer, leaving the other of the electrically insulating internal layer and the electrically insulating external layer intact to mechanically support the portion of the electrically conductive wall that is electrically isolated from the remainder of the electrically conductive wall.

20. The feedthrough of claim 18, further comprising:
an electrically insulating filler material disposed in the closed contour groove.

* * * * *